(12) United States Patent
Conklin

(10) Patent No.: US 12,419,742 B2
(45) Date of Patent: Sep. 23, 2025

(54) METHOD FOR DELIVERING A SURGICAL HEART VALVE

(71) Applicant: Edwards Lifesciences Corporation, Irvine, CA (US)

(72) Inventor: Brian S. Conklin, Orange, CA (US)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 559 days.

(21) Appl. No.: 17/664,619

(22) Filed: May 23, 2022

(65) Prior Publication Data

US 2022/0280290 A1     Sep. 8, 2022

Related U.S. Application Data

(63) Continuation of application No. 16/252,140, filed on Jan. 18, 2019, now Pat. No. 11,337,805.

(Continued)

(51) Int. Cl.
*A61F 2/24* (2006.01)

(52) U.S. Cl.
CPC .... *A61F 2/2427* (2013.01); *A61F 2210/0014* (2013.01); *A61F 2220/0075* (2013.01)

(58) Field of Classification Search
CPC ............ A61F 2/2436; A61F 2210/0014; A61F 2220/0075; A61F 2/2427; A61B 17/3423; A61B 2017/3425; A61B 2017/3427
See application file for complete search history.

(56) References Cited

U.S. PATENT DOCUMENTS

| 528,759 A | 11/1894 | Bernhardt |
| 3,143,742 A | 8/1964 | Cromie |

(Continued)

FOREIGN PATENT DOCUMENTS

| DE | 29911694 U1 | 8/1999 |
| EP | 0125393 A1 | 11/1984 |

(Continued)

OTHER PUBLICATIONS

A. Sidiropoulos, et al., Stentless Porcine Bioprostheses for all Types of Aortic Root pathology, European Journal of Cardio-Thoracic Surgery, 1997:11:917-921.

(Continued)

*Primary Examiner* — Brooke Labranche
*Assistant Examiner* — Christina C Lauer
(74) *Attorney, Agent, or Firm* — Guy Cumberbatch

(57) ABSTRACT

Valve holders and introducers for delivering a prosthetic heart valve to an implant site are configured to facilitate insertion of prosthetic valves through small incisions or access sites on a patient's body. The valve holders can also be configured to reduce or eliminate the occurrence of suture looping or other damage to the prosthetic valve during implantation. A valve holder according to embodiments of the invention includes features that reduce or eliminate mistakes during implantation of the prosthetic valves, such as a handle that prevents implantation of the valve prior to proper deployment or adjustment of the holder. An introducer is provided which can facilitate temporary deformation of a nitinol prosthetic valve to pass between adjacent ribs of a patient without rib spreading. Valves are provided having a wireform and stiffener band made of materials that exhibit superelastic properties. Valve holders, introducers, and valves according to the various embodiments can be used in minimally invasive procedures, such as thoracotomy procedures.

20 Claims, 18 Drawing Sheets

Related U.S. Application Data

(60) Provisional application No. 62/620,581, filed on Jan. 23, 2018.

(56) References Cited

U.S. PATENT DOCUMENTS

| | | |
|---|---|---|
| 3,164,009 A | 1/1965 | Schaschl |
| 3,320,972 A | 5/1967 | High et al. |
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 4,016,867 A | 4/1977 | King et al. |
| 4,035,849 A | 7/1977 | Angell et al. |
| 4,056,854 A | 11/1977 | Boretos et al. |
| 4,062,911 A | 12/1977 | Pepping |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,185,638 A | 1/1980 | Bruner |
| 4,211,241 A | 7/1980 | Kaster et al. |
| 4,217,665 A | 8/1980 | Bex et al. |
| 4,218,782 A | 8/1980 | Rygg |
| 4,252,131 A | 2/1981 | Hon et al. |
| 4,259,753 A | 4/1981 | Liotta et al. |
| 4,340,091 A | 7/1982 | Skelton et al. |
| 4,343,048 A | 8/1982 | Ross et al. |
| 4,362,167 A | 12/1982 | Nicolai et al. |
| 4,364,126 A | 12/1982 | Rosen et al. |
| 4,372,743 A | 2/1983 | Lane |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,585,453 A | 4/1986 | Martin et al. |
| 4,602,911 A | 7/1986 | Ahmadi et al. |
| 4,605,407 A | 8/1986 | Black et al. |
| 4,626,255 A | 12/1986 | Reichart et al. |
| 4,629,459 A | 12/1986 | Ionescu et al. |
| 4,643,194 A | 2/1987 | Fogarty |
| 4,679,556 A | 7/1987 | Lubock et al. |
| 4,680,031 A | 7/1987 | Alonso |
| 4,685,474 A | 8/1987 | Kurz et al. |
| 4,687,483 A | 8/1987 | Fisher et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,898,155 A | 2/1990 | Ovil et al. |
| 4,914,097 A | 4/1990 | Oda et al. |
| 4,940,459 A | 7/1990 | Noce |
| 4,960,424 A | 10/1990 | Grooters |
| 4,993,428 A | 2/1991 | Arms |
| 5,010,892 A | 4/1991 | Colvin et al. |
| 5,011,481 A | 4/1991 | Myers et al. |
| 5,032,128 A | 7/1991 | Alonso |
| 5,037,434 A | 8/1991 | Lane |
| 5,042,161 A | 8/1991 | Hodge |
| 5,053,008 A | 10/1991 | Bajaj |
| 5,089,015 A | 2/1992 | Ross |
| 5,147,391 A | 9/1992 | Lane |
| 5,163,955 A | 11/1992 | Love et al. |
| 5,171,248 A | 12/1992 | Ellis |
| 5,197,979 A | 3/1993 | Quintero et al. |
| 5,236,450 A | 8/1993 | Scott |
| 5,258,023 A | 11/1993 | Reger |
| 5,290,300 A | 3/1994 | Cosgrove et al. |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,471,756 A | 12/1995 | Bolanos et al. |
| 5,476,510 A * | 12/1995 | Eberhardt ............ A61F 2/2427 606/1 |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,496,346 A | 3/1996 | Horzewski et al. |
| 5,500,016 A | 3/1996 | Fisher |
| 5,531,785 A | 7/1996 | Love et al. |
| 5,533,515 A | 7/1996 | Coller et al. |
| 5,545,214 A | 8/1996 | Stevens |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A * | 12/1996 | Stevens .................. A61F 2/2433 604/6.16 |
| 5,584,878 A | 12/1996 | Love et al. |
| 5,613,937 A * | 3/1997 | Garrison ................ A61B 90/50 600/215 |
| 5,618,307 A | 4/1997 | Donlon et al. |
| 5,626,607 A | 5/1997 | Malecki et al. |
| 5,628,789 A | 5/1997 | Vanney et al. |
| 5,653,749 A | 8/1997 | Love et al. |
| 5,662,705 A | 9/1997 | Love et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,716,417 A | 2/1998 | Girard et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,814,096 A | 9/1998 | Lam et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,843,177 A | 12/1998 | Vanney et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,885,228 A | 3/1999 | Rosenman et al. |
| 5,891,160 A | 4/1999 | Williamson, IV et al. |

(56) References Cited

U.S. PATENT DOCUMENTS

| | | |
|---|---|---|
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,928,281 A | 7/1999 | Huynh et al. |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,001,126 A | 12/1999 | Nguyen-Thien-Nhon |
| 6,010,511 A | 1/2000 | Murphy |
| 6,010,531 A | 1/2000 | Donlon et al. |
| 6,019,739 A | 2/2000 | Rhee et al. |
| 6,042,554 A | 3/2000 | Rosenman et al. |
| 6,042,607 A | 3/2000 | Williamson, IV et al. |
| 6,045,576 A | 4/2000 | Starr et al. |
| 6,050,973 A | 4/2000 | Duffy |
| 6,059,827 A | 5/2000 | Fenton, Jr. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,136,017 A | 10/2000 | Craver et al. |
| 6,166,184 A | 12/2000 | Hendriks et al. |
| 6,210,338 B1 | 4/2001 | Afremov et al. |
| 6,214,054 B1 | 4/2001 | Cunanan et al. |
| 6,264,611 B1 | 7/2001 | Ishikawa et al. |
| 6,319,281 B1 | 11/2001 | Patel |
| 6,322,526 B1 | 11/2001 | Rosenman et al. |
| 6,350,281 B1 | 2/2002 | Rhee |
| 6,350,282 B1 | 2/2002 | Eberhardt |
| 6,491,624 B1 | 12/2002 | Lotfi |
| 6,582,419 B1 | 6/2003 | Schoon et al. |
| 6,598,307 B2 | 7/2003 | Love et al. |
| 6,773,457 B2 | 8/2004 | Ivancev et al. |
| 6,802,860 B2 | 10/2004 | Cosgrove et al. |
| 6,846,324 B2 | 1/2005 | Stobie |
| 6,942,694 B2 | 9/2005 | Liddicoat et al. |
| 7,007,396 B2 | 3/2006 | Rudko et al. |
| 7,018,404 B2 | 3/2006 | Holmberg et al. |
| 7,037,333 B2 | 5/2006 | Myers et al. |
| 7,258,698 B2 | 8/2007 | Lemmon |
| 7,270,142 B2 | 9/2007 | Acosta |
| 7,351,197 B2 | 4/2008 | Montpetit et al. |
| 7,637,943 B2 | 12/2009 | Lemmon |
| 7,713,216 B2 | 5/2010 | Dubey et al. |
| 7,842,084 B2 | 11/2010 | Bicer |
| 7,998,151 B2 | 8/2011 | St. Goar et al. |
| 8,057,396 B2 | 11/2011 | Forster et al. |
| 8,308,798 B2 | 11/2012 | Pintor et al. |
| 8,323,337 B2 | 12/2012 | Gurskis et al. |
| 8,348,998 B2 | 1/2013 | Pintor et al. |
| 8,449,625 B2 | 5/2013 | Campbell et al. |
| 8,475,521 B2 | 7/2013 | Suri et al. |
| 11,026,719 B2 * | 6/2021 | Thoreson ............ A61M 25/0662 |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0055773 A1 | 5/2002 | Campbell et al. |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0191416 A1 | 10/2003 | Rosenman et al. |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0148017 A1* | 7/2004 | Stobie .................... A61F 2/2427 623/2.11 |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0215235 A1 | 10/2004 | Jackson et al. |
| 2004/0225355 A1 | 11/2004 | Stevens |
| 2004/0236411 A1 | 11/2004 | Sarac et al. |
| 2004/0237321 A1 | 12/2004 | Rudko et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137702 A1 | 6/2005 | Haug et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |

(56) References Cited

U.S. PATENT DOCUMENTS

| | | |
|---|---|---|
| 2005/0234546 A1 | 10/2005 | Nugent et al. |
| 2005/0240259 A1 | 10/2005 | Sisken et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0004398 A1 | 1/2006 | Binder et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0122692 A1 | 6/2006 | Gilad et al. |
| 2006/0136054 A1 | 6/2006 | Berg et al. |
| 2006/0144441 A1 | 7/2006 | Acosta |
| 2006/0149360 A1 | 7/2006 | Schwammenthal et al. |
| 2006/0154230 A1 | 7/2006 | Cunanan et al. |
| 2006/0155321 A1 | 7/2006 | Bressler et al. |
| 2006/0161249 A1 | 7/2006 | Realyvasquez et al. |
| 2006/0167543 A1 | 7/2006 | Bailey et al. |
| 2006/0195134 A1 | 8/2006 | Crittenden |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane et al. |
| 2006/0241743 A1 | 10/2006 | Bergin et al. |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271000 A1 | 11/2006 | Ranalletta et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287718 A1 | 12/2006 | Bicer |
| 2006/0287719 A1 | 12/2006 | Rowe et al. |
| 2006/0293745 A1 | 12/2006 | Carpentier et al. |
| 2007/0005129 A1 | 1/2007 | Damm et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244546 A1 | 10/2007 | Francis |
| 2007/0244558 A1 | 10/2007 | Machiraju |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2007/0299513 A1 | 12/2007 | Ryan et al. |
| 2008/0009746 A1 | 1/2008 | Forster et al. |
| 2008/0021546 A1 | 1/2008 | Patz et al. |
| 2008/0033543 A1 | 2/2008 | Gurskis et al. |
| 2008/0033544 A1 | 2/2008 | Lemmon |
| 2008/0065198 A1 | 3/2008 | Quintessenza |
| 2008/0119875 A1 | 5/2008 | Ino et al. |
| 2008/0154356 A1 | 6/2008 | Obermiller et al. |
| 2008/0208331 A1 | 8/2008 | McCarthy et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0069890 A1 | 3/2009 | Suri et al. |
| 2009/0093877 A1 | 4/2009 | Keidar et al. |
| 2009/0132036 A1 | 5/2009 | Navia |
| 2009/0182419 A1 | 7/2009 | Bolling |
| 2009/0192599 A1 | 7/2009 | Lane et al. |
| 2009/0192600 A1 | 7/2009 | Ryan |
| 2009/0192602 A1 | 7/2009 | Kuehn |
| 2009/0192603 A1 | 7/2009 | Kuehn |
| 2009/0192604 A1 | 7/2009 | Gloss |
| 2009/0192605 A1 | 7/2009 | Gloss et al. |
| 2009/0192606 A1 | 7/2009 | Gloss et al. |
| 2010/0152844 A1 | 6/2010 | Couetil |
| 2010/0161036 A1 | 6/2010 | Pintor et al. |
| 2010/0249661 A1 | 9/2010 | Righini et al. |
| 2010/0249894 A1 | 9/2010 | Oba et al. |
| 2010/0249908 A1 | 9/2010 | Chau et al. |
| 2010/0331972 A1 | 12/2010 | Pintor et al. |
| 2011/0022165 A1 | 1/2011 | Oba et al. |
| 2011/0040372 A1 | 2/2011 | Hansen et al. |
| 2011/0147251 A1 | 6/2011 | Hodshon et al. |
| 2011/0276128 A1* | 11/2011 | Cao ............... A61F 2/2409 623/2.11 |
| 2012/0065729 A1 | 3/2012 | Pintor et al. |
| 2012/0071968 A1 | 3/2012 | Li et al. |
| 2012/0141656 A1 | 6/2012 | Orr et al. |
| 2012/0150288 A1 | 6/2012 | Hodshon et al. |
| 2012/0290079 A1 | 11/2012 | Murad et al. |
| 2013/0053949 A1 | 2/2013 | Pintor et al. |
| 2013/0116777 A1 | 5/2013 | Pintor et al. |
| 2013/0150954 A1 | 6/2013 | Conklin |
| 2014/0039609 A1 | 2/2014 | Campbell et al. |
| 2014/0058194 A1 | 2/2014 | Soletti et al. |
| 2014/0079758 A1 | 3/2014 | Hall et al. |

FOREIGN PATENT DOCUMENTS

| | | |
|---|---|---|
| EP | 0143246 A2 | 6/1985 |
| EP | 2080474 A1 | 7/2009 |
| FR | 2681775 A1 | 4/1993 |
| GB | 2083362 A | 3/1982 |
| GB | 2137499 A | 10/1984 |
| SU | 1116573 A1 | 7/1985 |
| SU | 1697790 A1 | 12/1991 |
| WO | 8102098 A1 | 8/1981 |
| WO | 8705489 A1 | 9/1987 |
| WO | 9213502 A1 | 8/1992 |
| WO | 9418909 A2 | 9/1994 |
| WO | 9516410 A1 | 6/1995 |
| WO | 9640006 A1 | 12/1996 |
| WO | 9725003 A1 | 7/1997 |
| WO | 9741801 A1 | 11/1997 |
| WO | 9742871 A1 | 11/1997 |
| WO | 01/50985 A1 | 7/2001 |
| WO | 2007146261 A2 | 12/2007 |
| WO | 2010090720 A1 | 8/2010 |
| WO | 2010111621 A1 | 9/2010 |

(56) References Cited

FOREIGN PATENT DOCUMENTS

| WO | 2011097355 A2 | 8/2011 |
|---|---|---|
| WO | 2011106354 A1 | 9/2011 |

OTHER PUBLICATIONS

Krakow, "3F Therapeutics, Inc. Announces the First Clinical Implantation of the 3F Enable Aortic Heart ValveTM, a Patented, Sutureless Implantation, Replacement Heart Valve Intended to Save Valuable Surgery Time and Reduce Time Related Complications . . . " Healthcare Sales & Marketing Network News Feed, Jan. 18, 2005, pp. 1 2.

Medtronic, The Freestyle Aortic Root Bioprosthesis.

Neal D. Kon, MD, et al., Comparison of Implantation Techniques Using Freestyle Stentles Porcine Aortic Valve, The Society of Thoracic Surgeons 1995, pp. 857-862.

Sadowski, Jerzy; Kapelak, Boguslaw; Bartus, Krzysztof, "Sutureless Heart Valve Implantation—A Case Study," Touch Briefings, 2005, pp. 48-50.

Stephen Westaby, et al., Aortic Valve Replacement With the Freestyle Stentless Xenograft, The Society of Thoracic Surgeons 1995, pp. S422-S427.

Stephen Westaby, et al., Time-Related Hemodynamic Changes After Aortic Replacement With the Freestyle Stentless Xenograft, The Society of Thoracic Surgeons 1995, pp. 857-862.

Techniques for 3D Quantitative Echocardiography, University of Washington Cardiovascular Research & Training Center Cardiac Imaging Research Lab, pp. 1-5, Oct. 2003.

* cited by examiner

METHOD FOR DELIVERING A SURGICAL HEART VALVE

CROSS-REFERENCE TO RELATED APPLICATION

This application is a continuation of U.S. patent application Ser. No. 16/252,140, filed Jan. 18, 2019, now U.S. Pat. No. 11,337,805, which claims the benefit of U.S. Patent Application No. 62/620,581, filed Jan. 23, 2018, the entire contents all of which are incorporated by reference for all purposes.

BACKGROUND

Field

The present disclosure generally concerns medical devices, deployment mechanisms, and methods for deploying such medical devices. More specifically, the disclosure relates to surgical replacement of heart valves that have malformations and/or dysfunctions. The present disclosure also relates to prosthetic heart valves, and specifically, prosthetic mitral valves, which can be implanted through a minimal-sized incision. Embodiments of the invention relate to holders for facilitating the implantation of bioprosthetic replacement heart valves at native heart valves, for example, for a mitral valve replacement procedure. Embodiments of the invention also relate to methods of using the holders to facilitate implantation of prosthetic heart valves.

Description of Related Art

Referring first to FIG. 1, the human heart is generally separated into four pumping chambers, which pump blood through the body. Each chamber is provided with its own one-way exit valve. The left atrium receives oxygenated blood from the lungs and advances the oxygenated blood to the left ventricle through the mitral (or bicuspid) valve. The left ventricle collects the oxygenated blood from the left atrium and pushes it through the aortic valve to the aorta, where the oxygenated blood is then distributed to the rest of the body. Deoxygenated blood from the body is then collected at the right atrium and advanced to the right ventricle through the tricuspid valve. The right ventricle then advances the deoxygenated blood through the pulmonary valve and the pulmonary arteries to the lungs to again supply the blood with oxygen.

Each of the valves associated with the chambers of the heart are one-way valves that have leaflets to control the directional flow of the blood through the heart, and to prevent backflow of the blood into other chambers or blood vessels that are upstream of the particular chamber. For example, as described above, the mitral valve controls the flow of oxygenated blood from the left atrium to the left ventricle, while preventing blood flow back into the left atrium. The valves are each supported by an annulus having a dense fibrous ring attached either directly or indirectly to the atrial or ventricular muscle fibers. When a valve become diseased or damaged, leakage or regurgitation may occur, where some of the blood travels back upstream through the diseased or damaged valve, and the efficiency and/or general functionality of the heart may be compromised.

Various surgical techniques can be performed to repair or replace a diseased or damaged valve. In some valve replacement procedures, the leaflets of the diseased or damaged native valve are first removed to prepare the valve annulus for receiving the prosthetic replacement valve. FIG. 2 shows an example of one type of popular prosthetic replacement valve 1 that is a tissue-type bioprosthetic valve generally constructed with natural-tissue valve leaflets 2, made for example, from porcine tissue or bovine pericardium, or from synthetic leaflets, that are mounted on a surrounding valve stent structure 3. The shape and structure of the leaflets 2 is supported by a number of commissure posts 4 positioned circumferentially around the valve stent structure 3. In these valves, a biocompatible cloth-covered suture or sewing ring 5 can also be provided on an inflow end of the stent structure 3 of the valve 1, to facilitate easier attachment to the native valve annulus. Such prosthetic valves function much like natural human heart valves, where the leaflets coapt against one another to effect the one-way flow of blood.

When implanting a tissue type prosthetic valve as described above at a native valve annulus, a number of sutures may be involved in the attachment process, many of which may be pre-installed for providing a track on which the valve is advanced to and properly positioned at the implant site. Additional sutures may also be applied between the prosthetic valve and the heart walls after proper placement, to securely attach or hold the valve implant in place. Meanwhile, in some cases, the prosthetic valves are implanted through small access channels using one of various minimally invasive surgical procedures, where visibility at the implant site may be impeded or obstructed. In addition, depending on the direction of implantation, for example, with some mitral valve replacement procedures, commissure posts of the stent or frame, or other portions, of the prosthetic valve may be pointed distally and advanced on a blind side of the valve, thereby obstructing visibility of the posts or other portions during advancement and implantation.

Each of the above factors may lead to tangling of the sutures with the valve prosthesis, most commonly with the commissure posts of the frame, since the commissure posts provide a protrusion on which the sutures can easily loop around and tangle. This type of entanglement of sutures with prosthetic valves is referred to as "suture looping," which specifically refers to instances where a suture is inadvertently wrapped around one or more of the commissure post tips, where it can then migrate towards and damage the leaflets or interfere with proper leaflet coaptation or other valve operation when the sutures are tightened or secured, resulting in improper valve operation. In some cases, such tangling may not be apparent to the practitioner at the time of implantation, and will only be revealed some time later when valve operation is observed to be improper or other complications arise in the patient, in which case, it may be necessary to initiate another procedure to repair or replace the prosthetic valve.

In addition, many existing bioprosthetic valves are not amenable to implantation through a minimal-size incision, such as in thoracotomy procedures. Such procedures can require a surgical valve and its holder to fit through incisions of approximately 15-20 mm in its narrowest direction.

SUMMARY

Attempts have been made to resolve the issue of suture looping, some of which involve holders that hold the prosthetic valves during delivery of the valves to the native valve annulus. In one example, a holder has a mechanism that urges the commissure posts of the prosthetic valve radially inwardly during delivery, such that the ends of the commissure posts are pointed inwards, to reduce the possibility of sutures catching against or looping around the commissure posts. After the valve prosthesis is delivered to the implant site, the holder is removed thereby releasing and expanding the commissure posts to their original positions. However, such holders may not be amenable to minimally invasive surgical techniques as the holder and valve combination may have a high or large profile, for example with the entire holder system positioned outside the valve, or the holder may not pull in the commissures enough to reduce the valve profile.

Meanwhile, Edwards Lifesciences has developed a valve holder system that can be used in mitral valve replacement procedures to protect the valve from suture looping during valve implantation. The system includes monofilament sutures that attach to both the holder and the commissures of the prosthetic valve, so that the sutures run over the outflow end of the valve between the ends of the commissures. When the holder is actuated, a central post extends distally through the prosthetic valve between the leaflets and pushes against the sutures that run across the middle of the valve between the commissures, pushing the sutures distally and causing an angled tent-like or "umbrella" effect on the sutures. The pressure on the sutures deflects the commissures slightly inwardly, while also forming angled surfaces or tracks with the sutures that slope outwardly from the central post to the commissure posts. These angled surfaces deflect any other sutures that might otherwise be looped over a commissure or leaflet away from the prosthetic valve. However, this system may not be very amenable to a minimally invasive surgical approach. The system does not pull in the commissures enough to reduce the valve profile, and the central post of the holder adds to the overall height of the valve once deployed, hindering minimally invasive surgical procedures.

In addition to the above, many of the newer holder designs also incorporate many additional parts that must be assembled by the practitioner or other end user, which may also lead to additional complications. Some holders incorporate various mechanisms and line connections, such that a number of additional steps must be taken by the practitioner to operate the holders correctly. Many of these holders have proven to be too complicated and/or prone to user error. For example, some holders may allow valves to be implanted without requiring that its mechanism be activated or deployed prior to delivery, for example, holders that allow delivery without deploying its mechanism to urge the commissure posts radially inward prior to insertion. Consequently, when practitioners use these holders improperly, suture looping still commonly occurs, while the implant process may also be further complicated by issues arising from user error. Further, some holders may require the practitioner to manually adjust the tightening of the holder to the prosthetic valves. Tightening too little can make the holder ineffective to prevent suture looping, while over-tightening can risk breaking one or more sutures of the system or damaging the valve.

Accordingly, a new replacement valve holder includes built-in mistake-proofing to ensure the anti-suture looping mechanism is engaged. In some embodiments, the new replacement valve holder can be designed to enable surgeons to implant the valve through minimal incisions, such as in thoracotomy procedures.

In one example, to fit through a minimal size incision, such as a 15-20 mm incision, a valve and holder combination can be collapsible in at least one direction. However, such holders and valves may not include a mechanism to actively collapse the valve into the reduced size configuration for delivery. Accordingly, an introducer according to other embodiments of the invention can be used with collapsible surgical valves and/or holders to introduce them into narrow surgical incisions, such as thoracotomies.

Features of the present disclosure provide for new holder systems and methods of using the holder systems, which reduce or eliminate the occurrence of suture looping or other damage to the prosthetic valves during implantation, for example, for mitral valve replacement using minimally invasive procedures or other procedures. Operation of the holders is also simplified, whereby the valves are prevented from being implanted prior to deployment of the holders, for example, via a holder that automatically activates upon connection of a handle to the holder, thereby reducing or eliminating mistakes caused by user error. According to embodiments, the system cannot be implanted until the handle is attached and activates the system. The holders also provide for integrated alignment features or other safety features, such that over-deployment or under-deployment of the holders is prevented.

According to embodiments of the invention, holders for prosthetic valve delivery reduce or eliminate occurrences of suture looping and/or other damage to the valves when the valves are implanted, while the mechanisms for deploying these features are integrated into the holders in a way that reduces or eliminates mistakes in use and deployment.

According to embodiments of the invention, the prosthetic valve includes a wireform and stiffener band made of materials that exhibit superelastic properties, such as nitinol, so that the stiffener band can be ovalized to a high degree for delivery through a small surgical incision. In addition, the holder according to some embodiments includes flexible arms to allow the valve holder to deform along with the prosthetic valve when compressed for insertion through a small incision, such as in minimally invasive procedures.

In some embodiments, a mitral valve holder is provided that uses a linearly movable piston to pull in the commissures of the valve towards the center of the valve, thereby eliminating the risk of suture looping. The holder has mistake-proofing features that prevent the physician from implanting the valve without engaging the system. For example, attaching the handle to the valve holder causes the piston to translate and thereby activate the system. The valve holder is prevented from being implanted before the handle is attached to the system. In some embodiments, by collapsing or deforming the profile of the valve and the valve holder, the holder system can allow implantation of the valve through a small or minimal incision. According to some embodiments, an introducer is provided to aid in implanting replacement valves through a minimal size incision, for example, by aiding in collapsing or otherwise reducing the profile of the valve and/or valve holder. The introducer can be used, for example, with mitral and/or aortic surgical valves. In some embodiments, such an introducer can be relatively short and only long enough to pass the valve past a patient's ribs. In other embodiments, the introducer can be relatively long and, for example, act as an atrial retractor, forming a channel all the way to the implant site in the case of a mitral valve.

BRIEF DESCRIPTION OF THE DRAWINGS

Further features and advantages of the invention will become apparent from the description of embodiments using the accompanying drawings. In the drawings.

DETAILED DESCRIPTION

Disclosed herein are various tools, such as valve holders and introducers, for assisting in the delivery and implantation of prosthetic heart valves, such as mitral heart valves, at an implant site. Disclosed are also methods for preparing the prosthetic heart valves for such procedures. Also disclosed are valves having a wireform and stiffener band made of materials that exhibit superelastic properties, such as nitinol, so that the stiffener band can be ovalized to a high degree for delivery through a small surgical incision. Embodiments of the valve holders and valves reduce occurrences of various complications that may arise during implantation, while remaining simple for end users to use. By providing these improved valve holders and valves, damage to the prosthetic valves during surgical procedures can be reduced, and additional costs for extended or additional procedures and/or replacement valves can be avoided.

The valve holders disclosed herein are particularly useful for avoiding suture looping and other valve damage during advancement of the prosthetic valves to the implant sites, as well as during final suturing of the valves at the native valve annulus. In many existing mitral valve replacement procedures, commissure posts of the prosthetic valve point distally away from practitioners, and in the direction of valve advancement and may be more prone to suture looping or other entangling. For such procedures, valve holders according to embodiments of the invention can urge the commissure posts radially inwards toward a center of the valve to reduce or eliminate suture looping. The presented embodiments can also include features that prevent valve implantation until the valve holders are in the activated or deployed positions. The holders can also include alignment features that prevent over-deployment or under-deployment. In this fashion, the holders provide ease of use while minimizing user errors.

Figure 1:
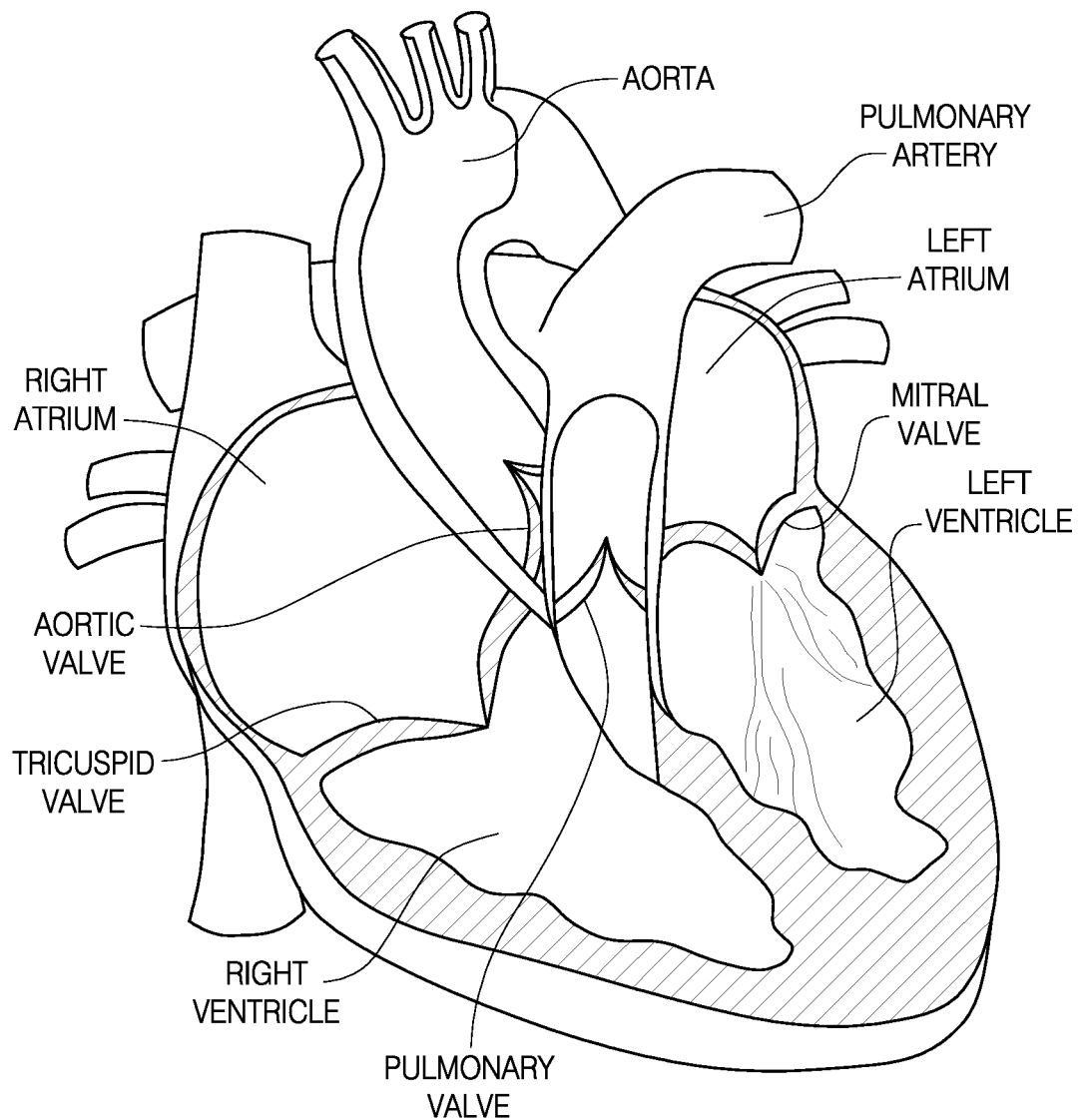
FIG. 1 shows a schematic cross-sectional view of a human heart.
Figure 2:
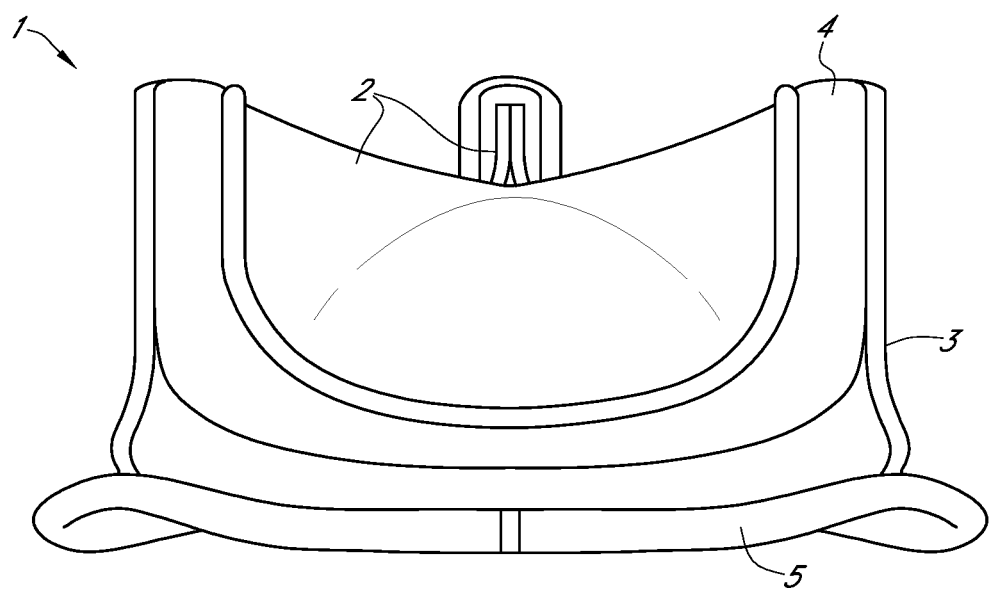
FIG. 2 shows a schematic perspective view of an example of a prosthetic valve that can be used with embodiments of the invention.

The disclosed mitral valve holder and handle system is specifically designed to address shortcomings in previous valve holders. The disclosed system prevents clinicians from forgetting or neglecting to deploy the system by means of a handle that deploys the valve holder upon attachment of the handle. Specifically, the disclosed valve holder system deploys automatically when the clinician attaches the handle to the valve holder, thereby preventing implantation before the system is deployed. The valve holder is unable to be implanted until the handle is attached, thereby enhancing safety of surgical procedures. In addition, the disclosed system becomes fully deployed upon attaching the handle, thereby preventing under-deployment or over-deployment of the system and damage to the valve or the sutures. As such, attachment of the handle to the valve holder provides mistake-proof deployment of the system as an automatically-deploying suture looping protection mechanism. The mechanism deploys when the handle is attached to it, thereby eliminating extra steps of deployment of the valve and adding a degree of mistake-proofing. Further, the disclosed valve holder allows the valve to be compressed to fit through a minimal size incision such as a thoracotomy. The prosthetic valve, for example, a prosthetic valve that is structurally similar to the prosthetic valve shown in FIG. 2, can be made of a nitinol wireform and nitinol stiffener band exhibiting a large amounts of flexibility to temporarily compress or deform the valve to fit through a minimal size incision.

Figure 3:
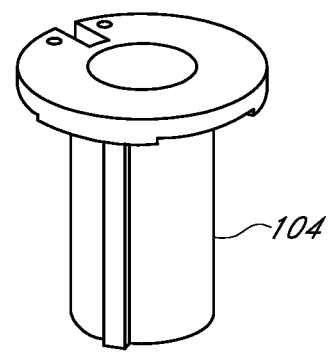
FIG. 3 shows an exploded perspective view of a valve holder for a prosthetic mitral valve according to an embodiment of the invention.
Figure 3:
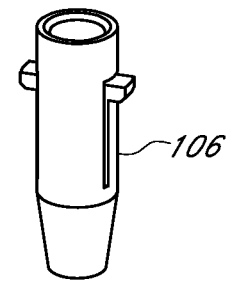
Figure 3:
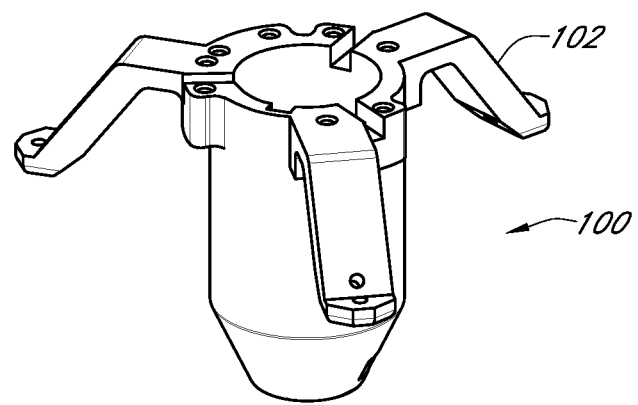
Figure 3:
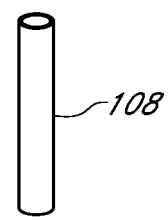
Figure 3:
Figure 4:
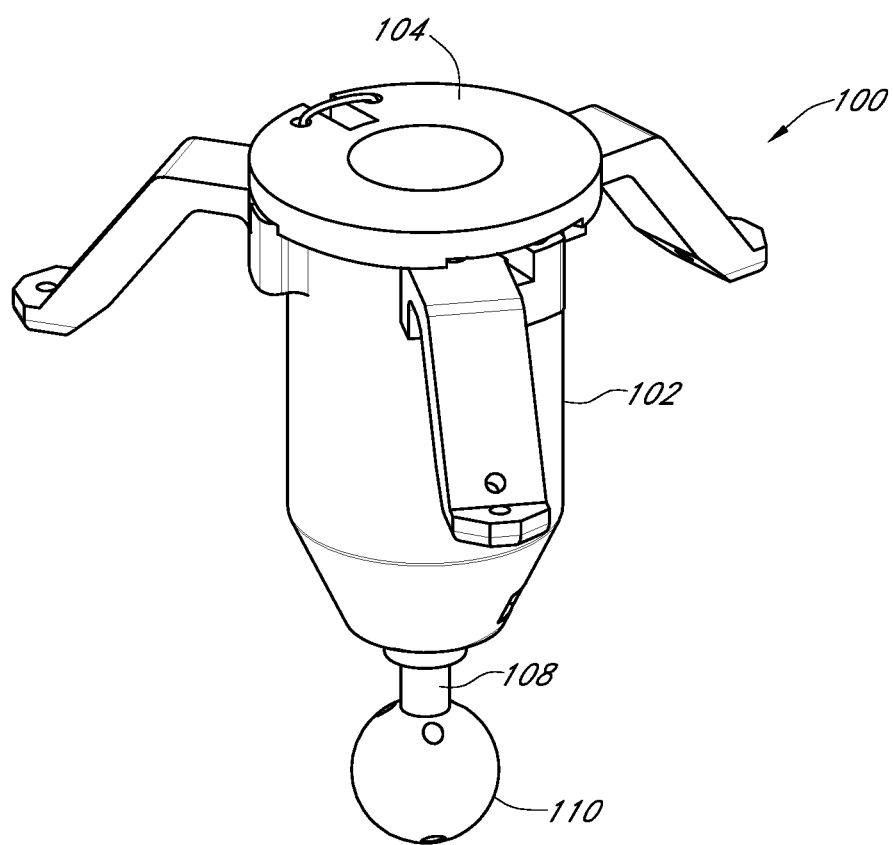
FIG. 4 shows a perspective view of the valve holder of FIG. 3 in an assembled state.
Figure 5:
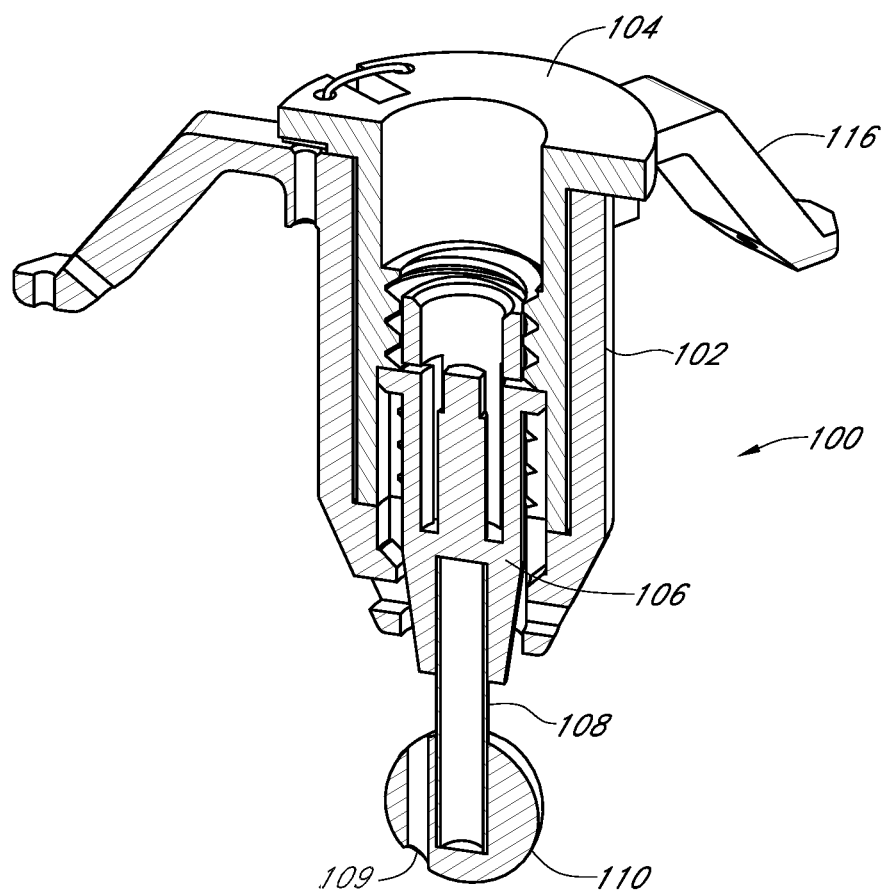
FIG. 5 shows a cross-sectional view of the valve holder of FIGS. 3 and 4.
Figure 6:
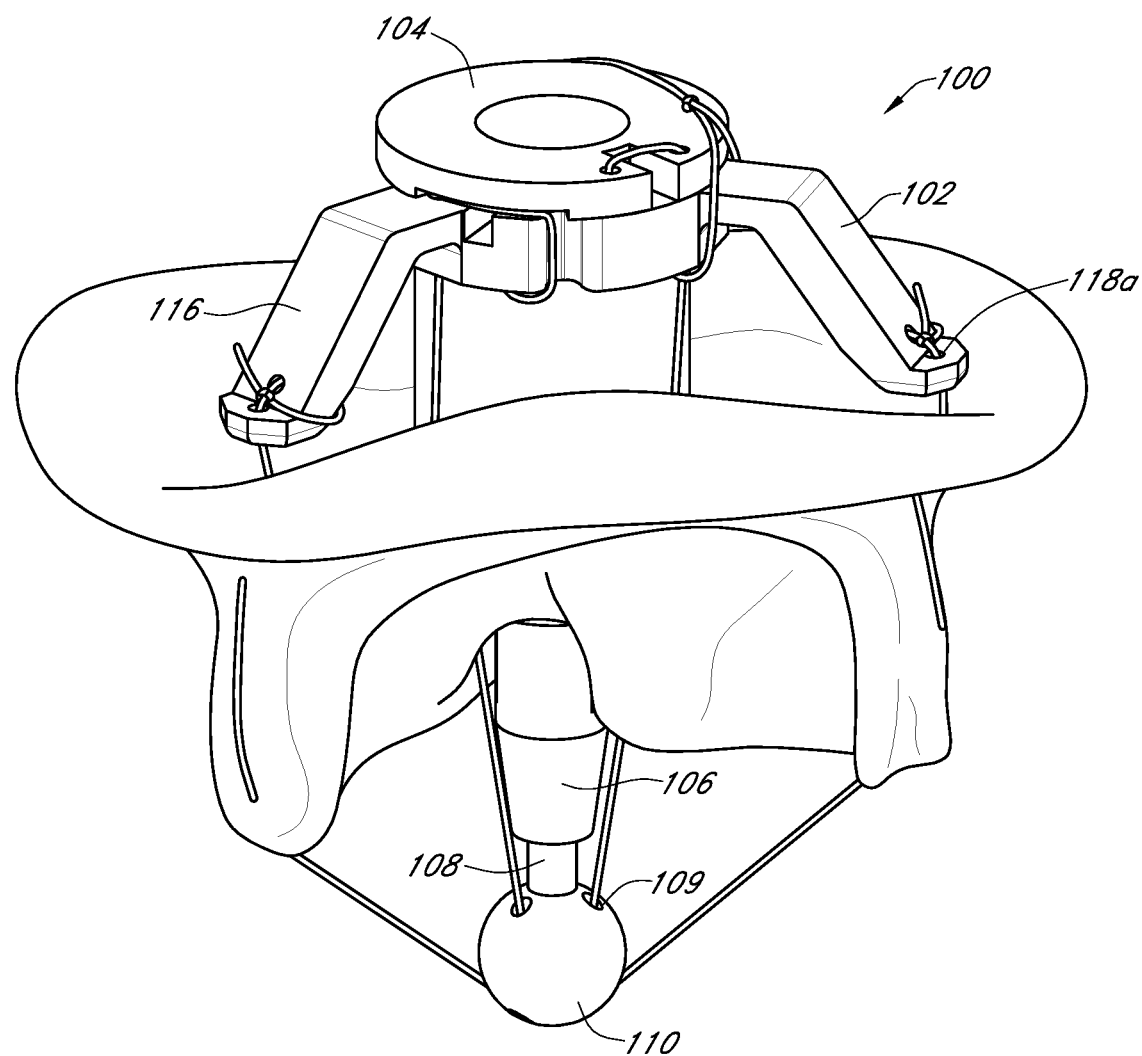
FIG. 6 shows a perspective view of the valve holder of FIGS. 3 to 5 in an assembled state with a prosthetic valve.

FIGS. 3 to 6 show views of a valve holder 100. FIG. 3 shows an exploded perspective view of the valve holder 100, FIG. 4 shows a perspective view of the valve holder 100 in an assembled state, FIG. 5 shows a cross-sectional view of the valve holder 100 in the assembled state, and FIG. 6 shows a perspective view of the valve holder 100 in the assembled state with an attached prosthetic valve.

The valve holder 100 includes a body 102, an insert 104, a piston 106, a shaft 108, and a suture mount 110. As described in more detail below, a prosthetic heart valve can be attached to the body 102. The insert 104 is positioned in a bore of the body 102 and connectable to a handle 112 to deploy or activate the valve holder 100 to adjust the prosthetic valve to a delivery or implantation position. The piston 106 is attached to the body 102 and to the insert 104. The piston 106 is movable from a first configuration where the valve holder 100 is un-deployed for connecting the prosthetic valve to the valve holder 100, to a second configuration where the valve holder 100 is deployed for implantation of the prosthetic valve in a heart of a human body. The shaft 108 is for connecting the piston 106 to the suture mount 110. The suture mount 110 is for routing sutures used to connect the valve holder 100 to the prosthetic valve.

Figure 7A:
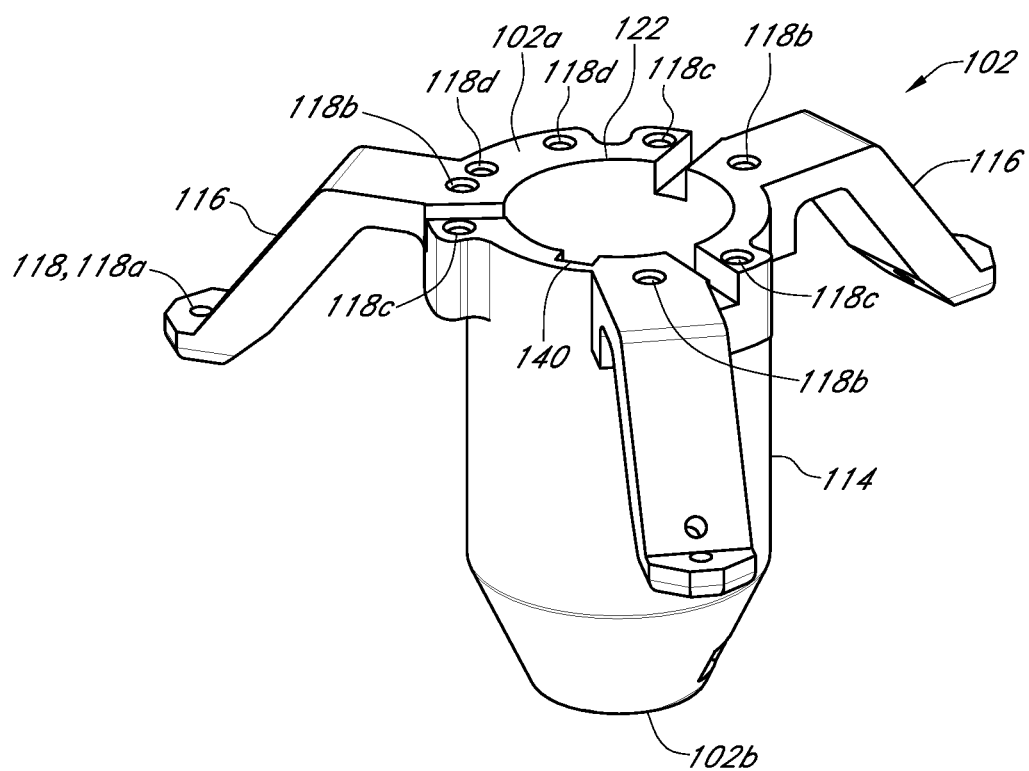
FIGS. 7A to 7B respectively show a perspective view and a cross-sectional view of a body of the valve holder of FIGS. 3 to 5.
Figure 7B:
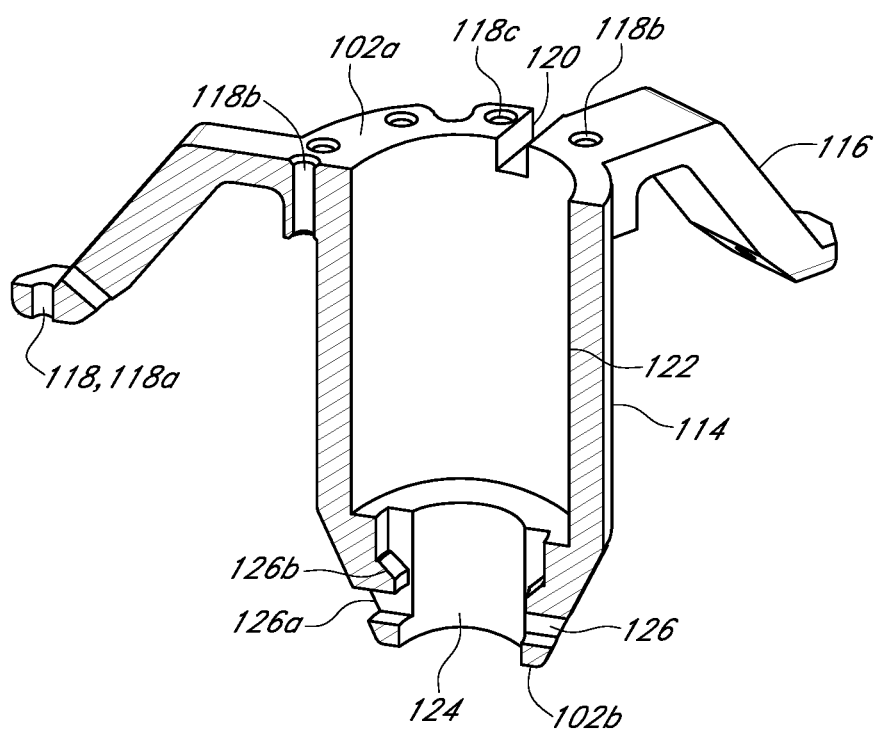

The body 102 of the valve holder 100 is shown in further detail in FIGS. 7A and 7B. The body 102 includes a generally cylindrically-shaped central hub 114 having a central axis, and a plurality of arms 116 extending from the central hub 114. The central hub 114 extends from a first proximal end 102a of the body 102 to a second distal end 102b of the body 102. The arms 116 serve as routing points for connecting commissure posts of the prosthetic valve to the valve holder 100 via sutures or other flexible material. The arms 116 are flexible and hinged relative to the central hub 114, and may be utilized as flexible living hinges during implantation. The flexible arms 116 allow the valve holder 100 to deform along with the prosthetic valve when compressed for insertion through a small incision, such as in minimally invasive procedures. In particular, the arms 116 are able to flex inward towards the hub 114, and laterally in some cases, to accommodate an ovalization of the valve as it is passed through a small surgical opening. Thereby, the valve and valve holder are able to pass through an opening about the size of a typical thoracotomy procedure without rib spreading, which may be approximately 20 mm in the narrowest direction. The flexible arms 116 may be resilient such that the flexible arms 116 may be deformed to fit through a small incision, and return to their original shape when the valve and valve holder 100 pass through the small incision.

In the embodiment shown, the body 102 includes three arms 116, but can include more or fewer arms 116 in other embodiments depending on the prosthetic valve the valve holder 100 is intended to hold. The number of arms 116 generally corresponds to the number of commissure posts on the prosthetic valve. When three arms 116 are included in the body 102, the arms 116 can be positioned around the body 102 at approximately 120 degrees relative to each other.

Each of the arms 116 includes one or more through holes or bores 118 for routing sutures connecting the valve holder 100 to the prosthetic valve. As will be further described below, the sutures are used to deploy or activate the valve holder 100 and place the valve in a delivery position where the commissure posts are urged radially inwards toward a center of the valve to reduce or eliminate suture looping. The through holes 118 extend transversely through the arms 116. The through holes 118 route the sutures across the top of the arms 116 (as illustrated) to a region below the arms 116 where the sutures can connect to tips of the commissure posts, for example, by passing the sutures over and/or through other portions of the valve. Multiple through holes 118 can be provided. Through holes 118a located near free ends of the arms 116 are used to route and position the sutures for connection to the commissure posts. Through holes 118b closer to the central hub 114 can be used to fasten or tie off an end of the sutures to the body 102, and to facilitate easier release of the valve from the valve holder 100. In some embodiments, through holes 118c on the central hub 114 may further be provided to facilitate easier release of the valve from the valve holder 100.

Referring to FIG. 6, the valve holder 100 may be connected to the prosthetic valve via sutures as follows. An end of the suture is fastened to the arms 116, for example, via a knot, and routed into the through holes 118a of the arms 116 near the free ends of the arms 116. The ends of the arms 116 are attached to the sewing ring of the valve via the suture, such that the flexible arms 116 can serve as living hinge areas to be compressed for implantation in minimally invasive surgical procedures. As shown in FIG. 6, the ends of the arms 116 may be respectively attached to the sewing ring of the valve at a single location. This attachment method, unlike previous valve holders which require two attachment points at each location, allows the arms 116 to pivot on the sewing ring when the system is deformed. The sutures are routed through the sewing ring of the valve, connected to the commissure posts of the valve, and routed through channels 109 of the suture mount 110. The sutures are then routed back through the valve and into through holes 118b, 118c located on or near the central hub 114. In some embodiments, a different number of through holes 118 can be provided for each suture, and in some embodiments, only one through hole 118 is provided for each suture, located on each respective arm 116.

Figure 12:
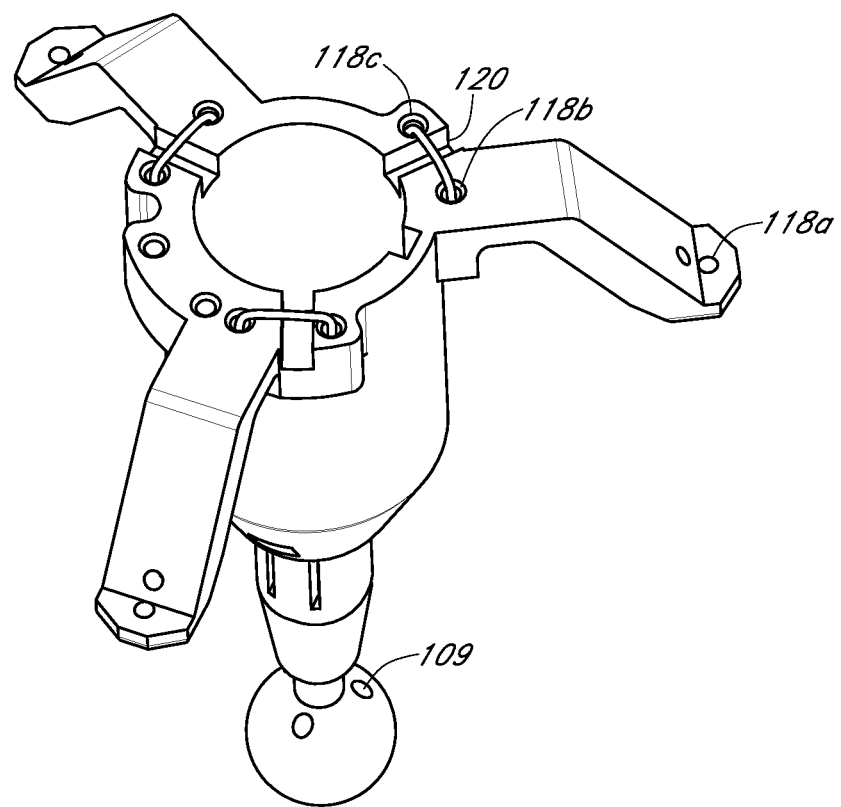
FIG. 12 shows a perspective view of the valve holder of FIGS. 3 to 5 in a deployed configuration with the insert removed.

An individual suture may be routed through both through holes 118b and 118c to provide a quick and easy method for removal of the valve from the valve holder 100 (see FIG. 12). At the first end 102a of the body 102, an upper surface of the central hub 114 includes a recess or slot 120 between the through holes 118b and 118c. The sutures extend across the recesses 120 such that there is a clearance underneath the sutures in the region of the recesses 120 to provide space for cutting the sutures. Cutting the sutures at the region of the recess 120 will release the valve from the valve holder 102. For example, when three arms 116 and three sutures are provided, the three sutures can be cut in the region of the recesses 120 to release the valve. If the valve is in the delivery position, cutting the sutures will also allow the commissures to spring back to a normal or unbiased geometry by releasing the commissure posts.

In use, the valve is designed to be placed over and/or around the second end 102b of the body 102 such that the body 102 is inserted into the valve. At the first end 102a, a bore 122 is provided in the central hub 114 for receiving the insert 104 therein. The bore 122 extends from the first end 102a and towards the second end 102b. Two through holes 118d are provided at the first end 102a for connecting the insert 104 to the central hub 114 via a single suture. A single suture connection to the insert 104 allows for quick and easy removal of the insert 104 from the body 102 by cutting the suture (see FIG. 6). At the second end 102b, an opening 124 is provided to allow a portion of the piston 106 to extend therethrough. An outer surface of the central hub 114 at the second end 102b may be tapered (e.g., may have a width or diameter that increases in a direction towards the first end 102a) to facilitate mounting of the valve or passing of the central hub 144 through the valve. The second end 102b additionally includes engagement portions 126 for connection to locks 128 of the piston 106. Each of the engagement portions 126 of the body 102 includes a channel 126a and a notch or protrusion 126b to facilitate engagement of the locks 128 of the piston 106, as further described below. The number of engagement portions 126 matches the number of locks 128 of the piston 106. In the embodiments shown, two engagement portions 126 and two locks 128 are provided. However, it should be appreciated that the number of engagement portions 126 and locks 128 may be varied in other embodiments.

Figure 8A:
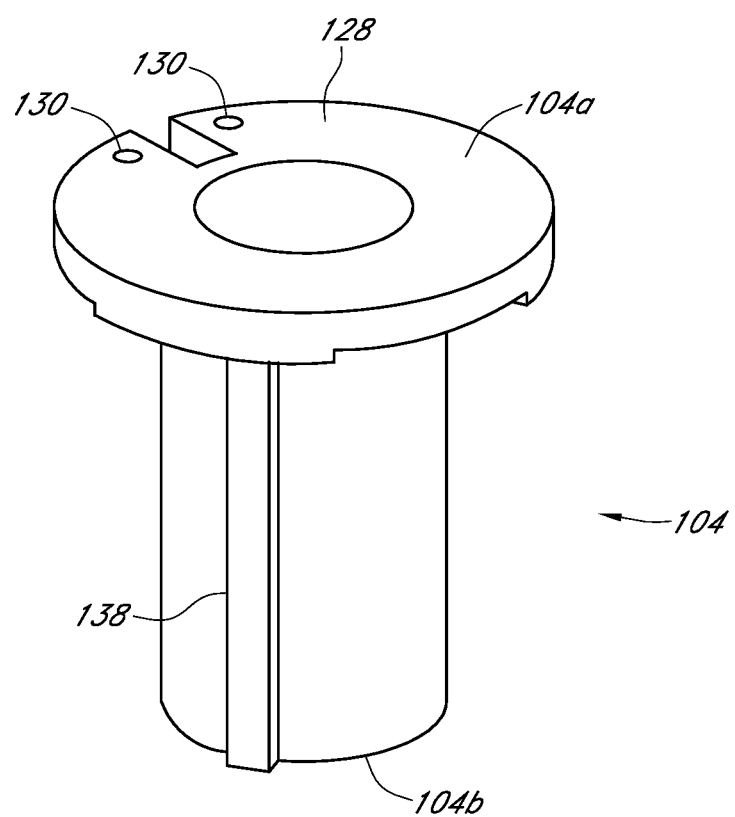
FIGS. 8A to 8B respectively show a perspective view and a cross-sectional view of an insert of the valve holder of FIGS. 3 to 5.
Figure 8B:
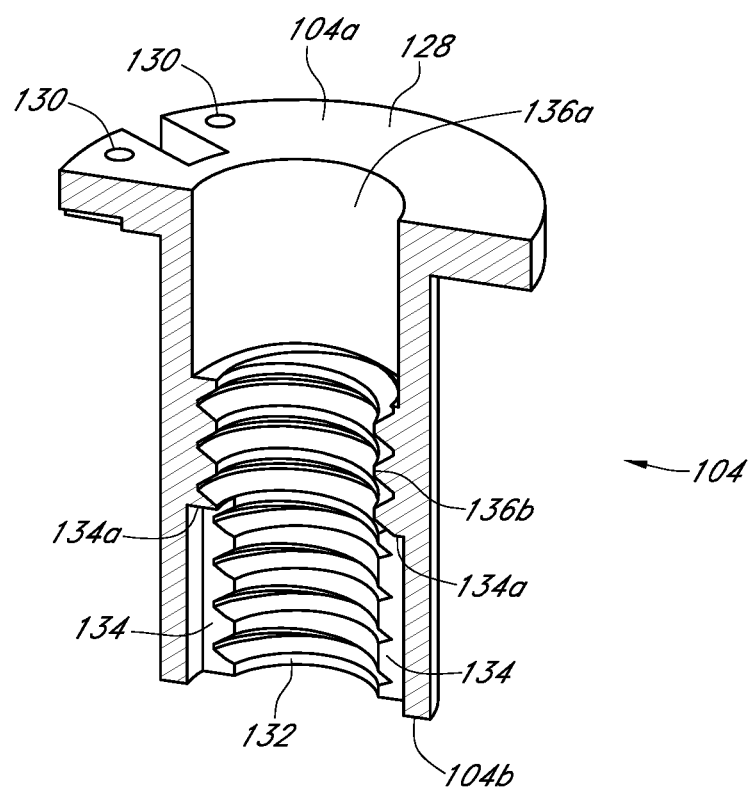

The insert 104 of the valve holder 100 is shown in further detail in FIGS. 8A and 8B. The insert 104 has a generally cylindrical shape with a flange 128 at a first proximal end 104a. The flange 128 includes two through holes 130 for communicating with the through holes 118d of the body 102 to connect the insert 104 to the body 102 via a single suture. The flange 128 may cover the other sutures discussed above that hold the body 102 to the valve, thereby preventing the holder 100 from being inadvertently or unintentionally released from the valve when, for example, releasing the insert 104 and the handle 112 from the body 102.

The insert 104 further includes a central opening 132 that extends through the insert 104 from the first proximal end 104a to a second distal end 104b, and a central axis. The insert 104 is configured to be received in the bore 122 of the body 102 such that the central axis of the insert 104 is aligned with (e.g., collinear with) the central axis of the body 102. The second end 104b of the insert 104 is designed to receive the piston 106 therein. The second end 104b includes slots or channels 134 extending towards the first end 104a to provide clearance for the locks 128 of the piston 106. The number of slots 134 matches the number of locks 128 of the piston 106. The insert 104 additionally includes an unthreaded lead-in portion 136a at the first end 104a followed by a threaded portion 136b for connection to the handle 112. The threaded portion 136b extends towards the second end 104b. The unthreaded portion 136a acts as a guide when inserting the handle 112 into the insert 104 to ensure proper alignment between the two parts before threading begins. This will greatly reduce the chances of cross-threading between the parts and generating undesirable particles. In addition, an outer surface of the insert 104 may include a key 138 for mating with a keyway 140 of the body 102. The key 138 and keyway 140 enable proper alignment of the insert 104 relative to the body 102.

Figure 9A:
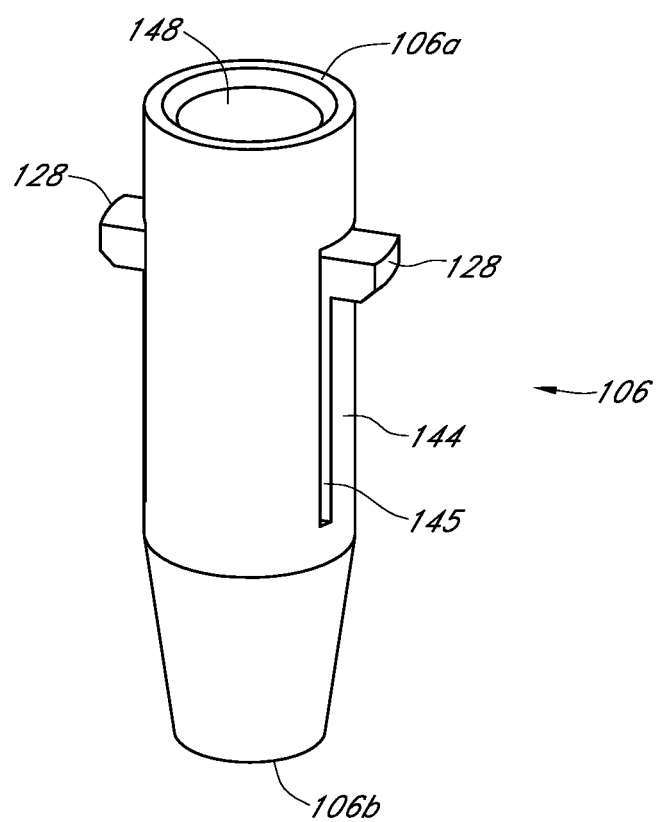
FIGS. 9A to 9B respectively show a perspective view and a cross-sectional view of a piston of the valve holder of FIGS. 3 to 5.
Figure 9B:
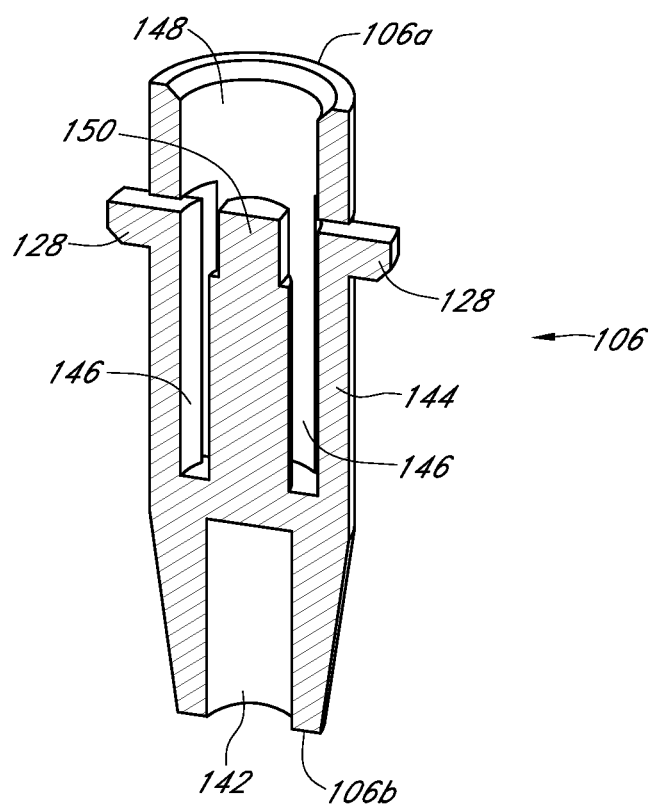

The piston 106 of the valve holder 100 is shown in further detail in FIGS. 9A and 9B. The piston 106 has a generally cylindrical shape from a first proximal end 106a to a second distal end 106b. The second end 106b includes a bore 142 for receiving a portion of the shaft 108 therein. An outer surface of the piston 106 at the second end 106b may be tapered (e.g., may have a width or diameter that increases in a direction towards the first end 106a). Meanwhile, the outer surface of the piston 106 includes the locks 128 for connection to the engagement portions 126 of the body 102. The locks 128 are provided on flexible arms 144 of the piston 106 that extend in a direction towards the first end 106a. In some embodiments, the locks 128 may be shaped as outwardly facing protrusions configured to be received in the channels 126a of the body 102. In some embodiments, the locks 128 of the piston 106 may be shaped as openings configured to receive inwardly facing protrusions of the body 102. The flexible arms 144 are spaced apart from the remainder of the piston 106 by gaps 145 on either side of the flexible arms 144 such that the flexible arms 144 are movable (e.g., bendable) relative to the other parts of the piston 106. The flexible arms 144 may be bent inwards relative to the other parts of the piston 106 and towards or into a cavity 146 of the piston 106. The flexible arms 144 may be resilient such that the arms 144 can be deflected inwards and then released, causing the arms 144 to spring back outwards to a relaxed shape when no longer deflected. In addition, the first end 106a of the piston 106 includes a bore 148 for connection to a tip portion 152 of the handle 112. The piston 106 also includes a central post 150 that acts as a stop for the tip portion 152 of the handle 112.

The suture mount 110 is used for suture routing. The suture mount 110 has a plurality of channels 109 extending from a first end 110a of the suture mount to a second end 110b of the suture mount (see FIGS. 10 and 12). The number of channels 109 generally corresponds to the number of commissure posts on the prosthetic valve. As described above, each channel 109 is used for routing a suture between one of the commissure posts of the valve and the central hub 114 of the body 102. As described in further detail below, the suture mount 110 may be moved distally (e.g., in a direction away from the first end 102a of the body 102) to urge the commissure posts downward and radially inwards toward a center of the prosthetic valve. In addition, the first end 110a of the suture mount 110 has a bore 111 to connect to the shaft 108. In some embodiments, the suture mount 110 may have a generally spherical shape, but is not limited thereto or thereby.

The shaft 108 is used to connect the piston 106 to the suture mount 110. The shaft 108 may be connected to the bore 111 of the suture mount 110 via a press fit, interference fit, through fasteners such as a set screw, and/or via an adhesive or the like. Similarly, the shaft 108 may be connected to the bore 142 of the piston 106 via a press fit, interference fit, through fasteners such as a set screw, and/or via an adhesive or the like. It should be appreciate that the shaft 108 may be connected to the piston 106 via a different type of connection than is used to connect the shaft 108 to the suture mount 110. For example, the shaft 108 may be connected to the piston 106 via an adhesive, and the shaft 108 may be connected to the suture mount 110 via a set screw.

The valve holder 100 may be assembled according to some embodiments as follows. The piston 106 may be inserted into the body 102 at the first end 102a, and moved distally such that the piston 106 extends out of the second end 102b of the body 102. In some embodiments, the suture mount 110 may have a larger diameter or width than the opening 124 of the second end 102b of the body 102, such that the suture mount 110 cannot be attached to the valve holder 100 until after the piston 106 is inserted into the body 102. In some embodiments, the piston 106 may be preassembled with the shaft 108 such that the piston 106 and the shaft 108 are inserted together into the body 102. In other embodiments, the shaft 108 may be connected to the piston 106 after the piston 106 is inserted into the body 102. The opening 124 of the body 102 is larger than the maximum diameter or width of the shaft 108 such that the shaft 108 may be inserted therethrough. In some embodiments, the suture mount 110 may have a smaller maximum diameter or width than the opening 124 of the body 102, such that the piston 106, the shaft 108, and the suture mount 110 may be preassembled, and all three components may be inserted together into the body 102. After the piston 106 is inserted into body 102 and the shaft 108 and suture mount 110 are connected, the valve may be connected to the body 102 and the suture mount 110 via sutures as described above. Subsequently, the insert 104 may be inserted into the body 102 and connected to the body 102 using a single suture as described above. The insert 104 is inserted into the body 102 such that the key 138 of the insert 104 is aligned with the keyway 140 of the body 102, and such that the slots 134 of the insert 104 are aligned with the locks 128 of the piston 106. In some embodiments, the slots 134 of the insert 104 permit translation of the piston 106 relative to the insert 104, but restrict or prevent rotation of the piston 106 relative to the insert 104. Further, in some embodiments, the insert 104 may be inserted into the body 102 before connecting the prosthetic valve to the valve holder 100.

Figure 10:
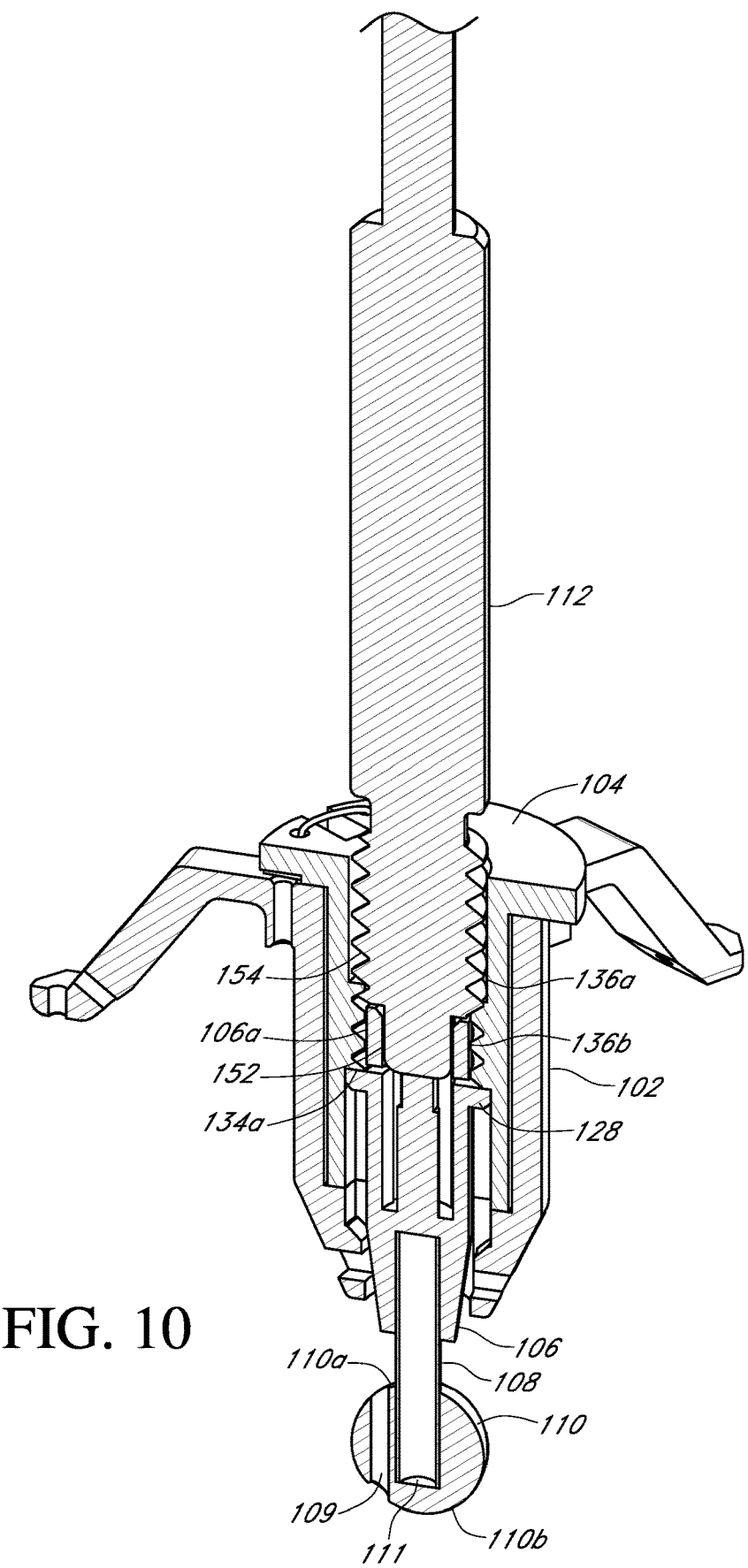
FIG. 10 shows a cross-sectional view of the valve holder of FIGS. 3 to 5 in an undeployed configuration.
Figure 11:
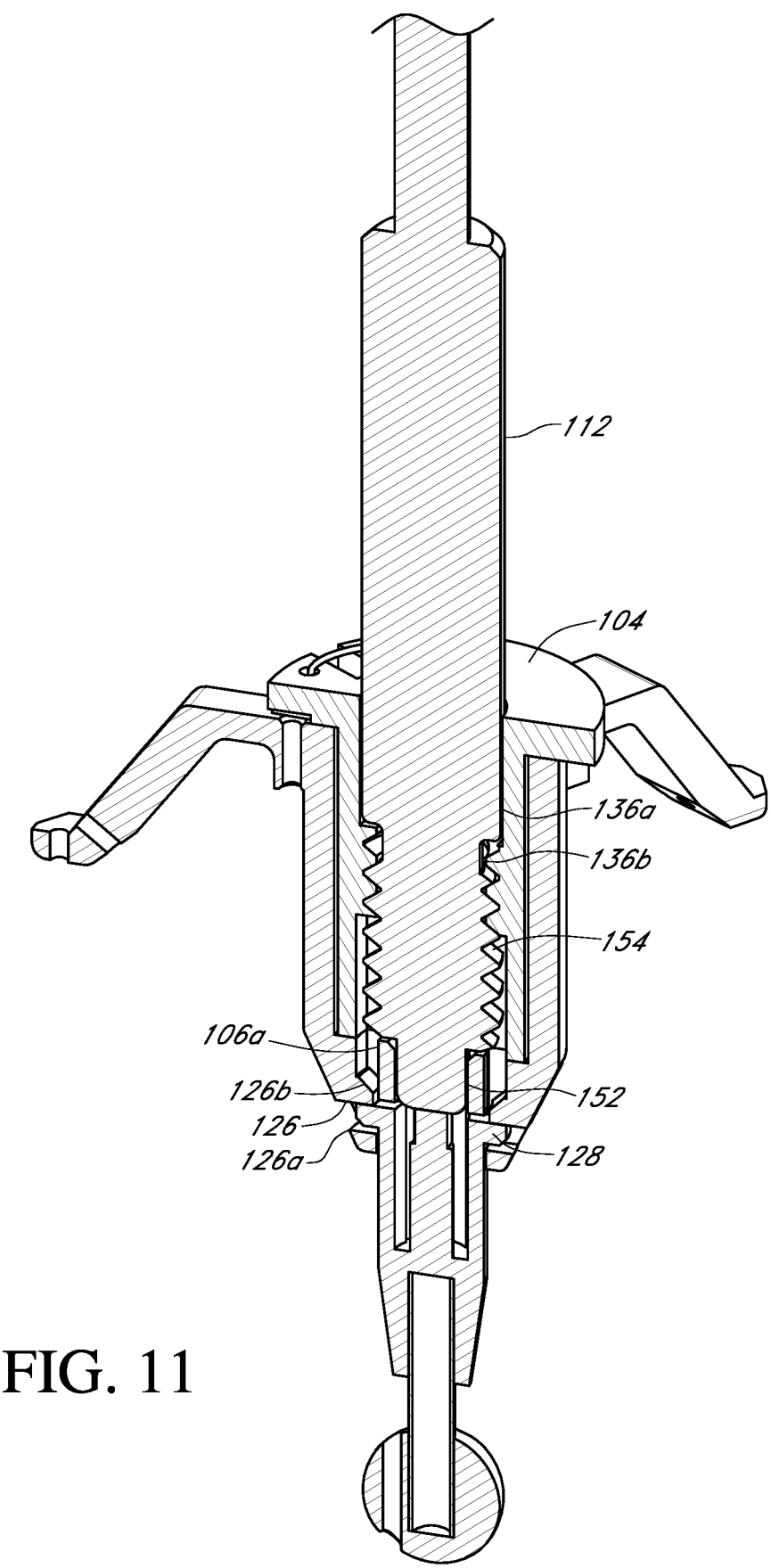
FIG. 11 shows a cross-sectional view of the valve holder of FIGS. 3 to 5 in a deployed configuration.

Referring to FIGS. 10 and 11, the valve holder 100 may be moved between a first configuration for connecting the prosthetic valve to the valve holder 100, and a second configuration where the prosthetic valve is in a collapsed or delivery position for implantation of the valve.

In the first configuration as shown in FIG. 10, the piston 106 is recessed relative to the body 102 such that the locks 128 of the piston 106 are adjacent or near end portions 134a of the slots 134 of the insert 104, for connection to the handle 112 having a tip portion 152 and a threaded portion 154. In the first configuration, the handle 112 can be inserted into the insert 104 and advanced distally until the tip portion 152 contacts or is positioned in the bore 148 of the piston 106 and the threaded portion 154 is adjacent or positioned in the unthreaded lead-in portion 136a of the insert 104. In other words, the threaded portion 154 of the handle 112 will first reach the unthreaded lead-in portion 136a of the insert 104 before reaching the threaded portion 136b of the insert 104. The unthreaded portion 136a helps prevent potential cross threading and particle generation by ensuring axial alignment of the handle 112 and the threaded portion 136*b* of the insert 104. In some embodiments, the threaded portion 154 of the handle 112 may have a thread size of, for example, #10-24 or M5.

When the valve holder is in the first configuration, the handle 112 can be screwed into the valve holder 100 to actuate the anti-suture-lopping mechanism. In particular, the handle 112 can be screwed in such that the threaded portion 154 of the handle 112 engages the threaded portion 136*b* of the insert 104. In so doing, the tip portion 152 of the handle 112 will axially press against the piston 106 to cause the piston 106 to move distally away from the first end 102*a* of the body 102. When the sutures are connected to the suture mount 110, the axial movement of the piston 106 will create tension in the suture lines and cause the sutures to be pulled in the direction of the moving piston 106. Because the sutures are connected to the commissure posts of the prosthetic valve, this distal pulling force activates or deploys the valve holder 100 to adjust the prosthetic value to a collapsed or delivery position by transferring the force onto the commissure posts of the prosthetic valve. The commissure posts are thereby radially urged inwards toward a center of the prosthetic valve.

The handle 112 can continue to be screwed into the valve holder 100 to reach a second configuration in FIG. 11, where the locks 128 of the piston 106 engage the engagement portions 126 of the body 102. Thereby, the locks 128 of the piston 106 will be pressed against the notches 126*b* of the engagement portions 126 to move into engagement with the channels 126*a*. In some embodiments where the locks 128 of the piston 106 include outwardly extending protrusions, the locks 128 will deflect inwards upon contact with the notches 126*b*, and snap into the channels 126*a*. The notches 126*b* of the body 102 may have a tapered shape widening towards the first end 102*b* to facilitate deflection of the locks 128 of the piston 106. In the second configuration, the piston 106 is in a fully extended position relative to the body 102 such that the first end 106*a* of the piston 106 is at a maximum distance away from the first end 102*a* of the body 102. By the engagement of the locks 128 of the piston 106 with the channels 126*a* of the body 102 in the second configuration, the piston 106 is prevented or hindered from moving back towards the first configuration, thereby enhancing safety of the valve holder 100. That is, the engagement of the locks 128 and the channels 126*a* act as a stop to prevent or hinder relative motion between the piston 106 and the body 102 while in the second configuration. Safety of procedures using the holder 100 is also enhanced because the valve holder 100 becomes automatically deployed when connecting the handle 112 to the valve holder 100. In addition, the locations of the piston 106 and the suture mount 110 in the second configuration are designed to place a desired amount of tension in the suture lines to radially urge the commissure posts of the valve inwards to a predetermined degree. Safety is thus further enhanced by eliminating over-tightening or under-tightening of the valve. By fully threading the handle 112 into the valve holder 100 (e.g., by bottoming out the handle 112, or at least until the piston 106 snaps into the second configuration), the valve holder 100 will automatically achieve the desired amount of tightening of the valve. Meanwhile, safety is further enhanced because the valve holder 100 is prevented from being implanted until the handle 112 is connected and the valve holder 100 is in the second configuration. In addition, the various components of the valve holder 100 can be preassembled prior to use in surgical procedures, as described above.

Upon implantation to a desired location in a patient, the insert 104 can be disconnected and removed from the valve holder wo by cutting the single suture connecting the insert 104 to the body 102 (see FIG. 6). Thereby, the handle 112 and the insert 104, which are threadably connected, can be removed together from the rest of the valve holder 100. Safety of the valve holder 100 is enhanced because the flange 128 of the insert 104 blocks the other sutures connecting the valve to the holder 100 to prevent the holder wo from being inadvertently or unintentionally released from the valve until the insert 104 is removed. Once the insert 104 is removed, final adjustments and implantation steps can be taken to implant the prosthetic vale at the implant site, and the valve holder 100 can then be disconnected and removed from the valve afterwards by cutting the sutures connecting the body 102 to the valve (see FIG. 12).

Meanwhile, various different features from the different embodiments discussed above can also be combined into a single modified valve holder. In addition, various other modifications or alternative configurations can also be made to the valve holder according to the above described embodiments of the invention.

The presented embodiments further include a prosthetic valve exhibiting a large amount of flexibility for use in minimally invasive surgical procedures. The prosthetic valve can be made of a wireform and stiffener band exhibiting large amounts of flexibility to temporarily compress or deform the valve to fit through a minimal size incision, and revert to its uncompressed state after passing through the minimal size incision. In particular, the wireform and the stiffener band can be made of a material exhibiting superelastic properties, such as nitinol. However, other materials may be used that can withstand high amounts of elastic strain and provide sufficient radial stiffness. In some embodiments, the stiffener band exhibiting superelastic properties can be ovalized to a high degree for delivery through a small surgical incision of approximately 15-20 mm by 45-50 mm, and the stiffener band can be returned to it its original circular shape, while maintaining circularity of the valve during manufacture and after implantation. Such wireforms and stiffener bands having superelastic properties can be used in replacement of existing cobalt-chrome or cobalt-chromium (CoCr) wireforms and stiffener bands, which do not permit ovalization for delivery through minimally invasive procedures.

In some embodiments, a nitinol stiffener band can have the same radial stiffness as existing prosthetic valves utilizing CoCr stiffener bands. For example, nitinol may have an initial elastic modulus that is approximately 40% of the elastic modulus for CoCr alloys used in prosthetic valves. The resistance to radial force can be matched between the nitinol stiffener band and an existing CoCr band by setting the product of their area moments of inertia and their Young's moduli equal. For example, for a 25 mm valve, a CoCr stiffener band may be approximately 0.0106" or 0.27 mm thick. Matching the stiffness in the initial elastic range of nitinol, would result in a thickness of about 0.0144" or 0.37 mm for a nitinol stiffener band based on an assumed Young's modulus for nitinol that is 40% of CoCr. Such a thickness for a nitinol stiffener band does not add significantly to the overall size of the valve, and permits the valve to be constructed similarly to existing prosthetic valves that utilize CoCr stiffener bands, while also being able to utilize a collapsible wireform and stiffener band that can be temporarily collapsed into an oval configuration of approximately 18 mm by 45 mm. Such a valve is able to fully recover to a circular configuration after passing through an introducer, as described above. In addition, the nitinol stiffener band can incorporate the commissure "towers" used with existing polyester bands, thereby also eliminating the need for the polyester bands and simplifying construction.

The disclosed stiffener band can be manufactured from a nitinol sheet using laser cutting, die cutting, photo etching, or other common methods of producing 2D parts from sheet material. Subsequently, the 2D parts can be formed into 3D circular parts by heat treatment methods for nitinol. The ends of the nitinol stiffener bands can be joined using laser or resistance welding, or could alternatively be temporarily joined using an elastic sleeve.

Some of the presented embodiments may also include an introducer which aids in delivering valve holders in minimally invasive surgical procedures. The introducer can be used with the collapsible surgical valves having superelastic properties described above to introduce the valves into a narrow surgical incision, such as a thoracotomy. The introducer can be used, for example, for delivering a prosthetic mitral valve to the mitral position. The introducer has a funnel-like shape for passing a collapsible heart valve from outside the body to inside the body through a narrow opening, such as the space between two ribs. In thoracotomy procedures, an incision is introduced into the chest cavity through the chest wall. In intercostal approaches, the incision is made between adjacent ribs to minimize cuts through bone, nerves, and muscle. In a typical thoracotomy procedure, the distance between the ribs, without spreading the ribs, is about 15 to 20 mm. Parallel to the ribs, the incision can be longer as needed, for example, approximately 45 mm or greater. Collapsible valve holders can have a small size that is particularly suited to fit in the small gap between the ribs in thoracotomy procedures.

Figure 13:
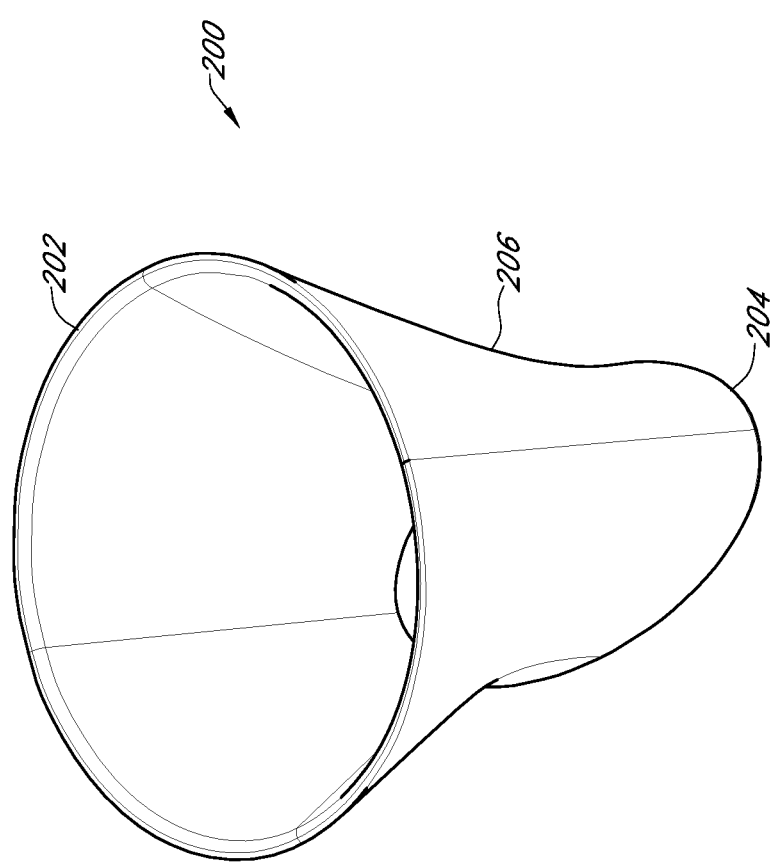
FIG. 13 shows a perspective view of an introducer for use with a valve holder.
Figure 14:
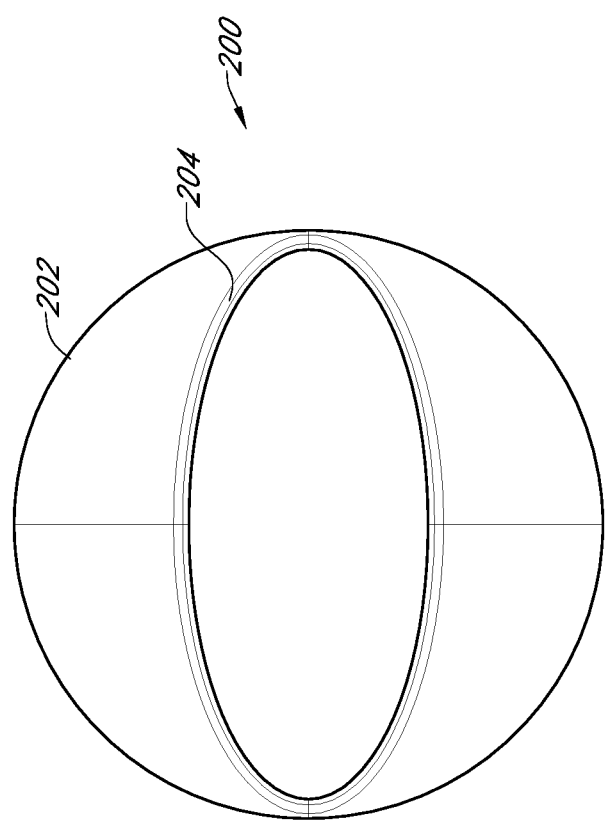
FIG. 14 shows a front view of the introducer of FIG. 13.

FIGS. 13 to 14 show views of an introducer 200 for introducing a valve and holder into a human body according to another embodiment. The introducer 200 provides a simple approach for implanting collapsible heart valves connected to flexible holders through a minimal size incision, such as in a thoracotomy procedure. Due to the small gap between human ribs, the introducer 200 is used as an aid for inserting valves mounted on flexible holders past the ribs and into the chest cavity during a thoracotomy or other minimally invasive procedures.

Figure 15:
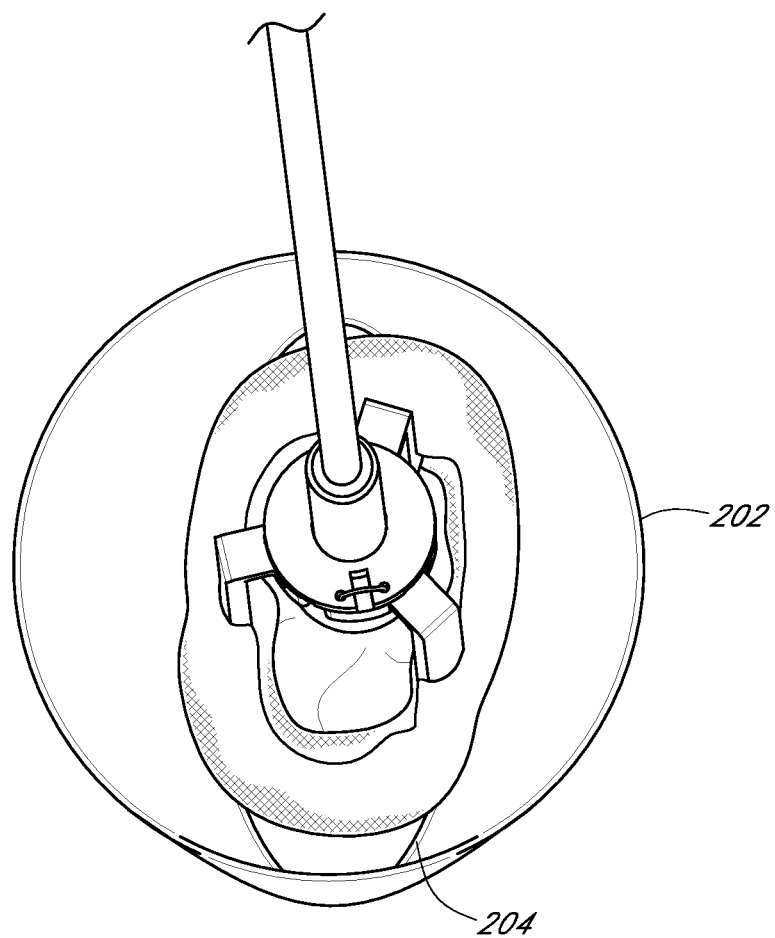
FIG. 15 shows a perspective view of the valve holder of FIGS. 3 to 5 in use with the introducer of FIGS. 13 and 14.

The introducer 200 has a hollow, funnel-like shape for receiving flexible holders with mounted valves, with a central axis of the valves pointed in a direction of insertion, for example, with an outflow end of the valve pointed or directed towards the introducer 200, as shown in FIG. 15. The introducer 200 has a first, proximal end 202, and a second, distal end 204. The distal end 204 of the introducer faces towards the incision during placement or positioning, while the proximal end 202 faces away from the incision and towards the operator of the holder. The proximal end 202 has a circular cross-sectional shape corresponding to the circular shape of the prosthetic heart valves. In use, the proximal end 202 is located outside of the incision. In one embodiment, the cross-section of the proximal end 202 is 45 mm in diameter. The distal end 204 has an oval cross-sectional shape corresponding to a size and shape of a surgical opening between ribs in a thoracotomy procedure. In one embodiment, the major diameter of the cross section of the distal end 204 is 45 mm in diameter and the minor diameter of the cross section is 15 to 20 mm in diameter. Between the proximal and distal ends 202, 204, the introducer 200 includes a smooth transition zone or region 206 connecting the ends 202, 204. The transition region 206 may have a smooth, continuous inner profile between the ends 202, 204, which is substantially free from corners.

The introducer 200 can be made very inexpensively as a disposable item that is supplied with a valve. The introducer 200 can be made of or include polypropylene, or any other suitable material having a low coefficient of friction. The introducer 200 can be a molded part. Meanwhile, the valve to be implanted can be made of a nitinol wireform band exhibiting a large degree of elasticity. In one embodiment, the valve exhibits superelastic properties.

In use, the introducer 200 is first introduced into an incision in the chest cavity with the distal end 204 positioned between two ribs. The valve, connected to a flexible holder, is inserted into the proximal end 202 of the introducer 200, as shown in FIG. 15. The valve is then pushed towards the smaller, distal end 204 of the introducer 200, where the valve elastically deforms to squeeze through the smaller cross-sectional shape. The valve can take on the oval shape of the introducer or another generally collapsed shape as it is pushed through the introducer 200, due to the superelastic properties of the valve. Once the valve clears the distal end 204 of the introducer 200, the valve regains its undeformed shape (e.g., its circular shape). In this way, the deformation of the valve and holder 100 is passive, being imposed or dictated by the shape of the introducer rather than by a mechanism on the holder itself. The advantage of this configuration is that the holder can be a very inexpensive molded component.

In one embodiment, a length of the introducer 200 is sufficient to introduce the valve into an internal surface of the chest wall past the rib cage. In such an embodiment, a length of the introducer from the proximal end 202 to the distal end 204 may be up to 40 mm long. In other embodiments, a length of the introducer can be made longer. In one embodiment, the distal end 204 could be extended many more centimeters so that it would extend, for example, into the left atrium of the heart, for a mitral valve replacement, to act as an atrial retractor. Meanwhile, the proximal end 202 of the introducer 200 can remain positioned outside of the incision in the chest cavity. This would provide a tunnel from the outside of the body all the way to the site of implantation at the mitral annulus.

In alternative embodiments, the introducer 200 can include various additional features, for example, a slit in a wall of the introducer 200 can be provided to give clearance for sutures passing through a side of the introducer during surgical procedures. In addition, lighting, such as light emitting diodes ("LEDs"), can be added to the introducer, along with a power supply, such as batteries, to power the lighting. LED lighting can be inexpensively added to the introducer with a built-in battery. The lighting can be particularly useful with the extended version of the introducer. The lighting can provide excellent illumination at the site of implantation and reduce the need for additional external lighting.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples and should not be taken as limiting the scope of the disclosure. Rather, the scope of the disclosure is defined by the following claims.

What is claimed is:

1. A method for delivering a surgical prosthetic heart valve to a native annulus via a thoracotomy, the method comprising:
   preparing a flexible prosthetic heart valve for delivery having an undeformed circular shape looking along a central axis, the heart valve comprising a superelastic flexible frame defining commissure posts extending distally from a proximal/inflow end of the heart valve and a plurality of flexible leaflets secured to the frame and forming occluding surfaces for one-way blood flow in an inflow to outflow direction, the proximal/inflow end of the heart valve being detachably coupled to a valve holder connectable to a delivery handle with the handle extending in a proximal direction away from the valve holder such that the heart valve points distally from the handle;
   creating an access pathway to the native annulus, including forming a thoracotomy incision between adjacent ribs;
   positioning an introducer funnel within the thoracotomy incision, the introducer funnel having a proximal end with a circular cross-sectional shape sized to receive the heart valve in an undeformed configuration and a smaller, distal end with an oval cross-sectional shape corresponding to a size and shape of the thoracotomy incision, wherein the introducer funnel has a smooth transition zone connecting the proximal and distal ends substantially free from corners;
   inserting the heart valve and valve holder using the handle into the proximal end of the introducer funnel;
   pushing the heart valve and valve holder using the handle towards the smaller, distal end of the introducer funnel to cause the heart valve to elastically deform and squeeze through the oval cross-sectional shape past the adjacent ribs and return to the undeformed circular shape; and
   advancing the heart valve and valve holder using the handle to the native annulus for implant therein.

2. The method of claim 1, wherein the adjacent ribs are spaced apart about 15 to 20 mm and the thoracotomy incision has a length of 45 mm or greater.

3. The method of claim 2, wherein the circular cross-sectional shape of the proximal end of the introducer funnel is 45 mm in diameter.

4. The method of claim 3, wherein the oval cross-sectional shape of the distal end of the introducer funnel has a major diameter of 45 mm and a minor diameter of 15 to 20 mm.

5. The method of claim 4, wherein the introducer funnel is molded of polypropylene.

6. The method of claim 1, wherein the introducer funnel is molded of polypropylene.

7. The method of claim 1, wherein the flexible frame of the heart valve is a nitinol wireform band.

8. The method of claim 1, wherein the flexible frame of the heart valve is a wireform and a stiffener band both exhibiting superelastic properties.

9. The method of claim 1, wherein the length of the introducer funnel is sufficient to advance the heart valve into an internal surface of the chest wall past the rib cage.

10. The method of claim 9, wherein the length of the introducer funnel is up to 40 mm long.

11. The method of claim 1, wherein the length of the introducer funnel is sufficient to advance the heart valve into the left atrium of the heart, and the native valve is a mitral valve.

12. The method of claim 1, wherein the proximal/inflow end of the heart valve has a biocompatible cloth-covered sewing ring configured to receive attachment sutures to attach the heart valve to the native valve annulus, and wherein the valve holder extends through a flow orifice of the heart valve and has a mechanism that engages the commissure posts of the flexible frame and is configured to flex the commissure posts radially inwards toward the central axis in a delivery position of the heart valve to reduce or eliminate suture looping of the attachment sutures around the commissure posts, the method including converting the heart valve to the delivery position prior to advancing the heart valve and valve holder using the handle to the native annulus for implant therein.

13. The method of claim 12, wherein the valve holder has a body detachably coupled to the sewing ring and a piston configured to be positioned at least partially in the body, the piston being configured to translate relative to the body along the central axis to adjust the heart valve to the delivery position.

14. The method of claim 13, wherein the wherein the body comprises a hub and a plurality of outwardly splayed arms that contact the sewing ring, the arms being flexible to allow the body to deform for insertion into a small surgical opening.

15. The method of claim 14, wherein the flexible arms of the body are configured to deform inwards in a direction towards the hub such that a maximum width of the body decreases when the arms are deformed.

16. The method of claim 14, wherein the flexible arms are resilient such that the arms are configured to deform upon the application of a force and return to their original shape when the force is removed.

17. The method of claim 13, wherein a proximal opening of the body comprises a threaded portion configured to mate to a threaded portion of the delivery handle.

18. The method of claim 17, wherein the delivery handle comprises a tip portion configured to engage an opening of the piston when the threaded portion of the handle mates with the threaded portion of the body to cause translation of the piston relative to the body.

19. The method of claim 13, further including a suture mount on a distal end of the piston, the suture mount having channels for routing connecting sutures used to detachably connect the valve holder to the heart valve.

20. The method of claim 19, wherein the connecting sutures are routed through the sewing ring of the heart valve, connect to the commissure posts of the valve, and routed through the channels of the suture mount and then back through the valve and tied to thee valve holder, wherein distal translation of the piston relative to the body pushes the connecting sutures distally and flex the commissure posts radially inwards.

\* \* \* \* \*